(12) United States Patent
Torres

(10) Patent No.: US 7,494,673 B1
(45) Date of Patent: Feb. 24, 2009

(54) METHOD FOR TREATMENT OF KIDNEY AND/OR URINARY SYSTEM STONES

(76) Inventor: Phillip Torres, 14444 SW. 46th Ter., Miami, FL (US) 33175-6834

( * ) Notice: Subject to any disclaimer, the term of this patent is extended or adjusted under 35 U.S.C. 154(b) by 0 days.

(21) Appl. No.: 12/002,404

(22) Filed: Dec. 17, 2007

Related U.S. Application Data

(63) Continuation-in-part of application No. 11/804,185, filed on May 17, 2007, now abandoned.

(51) Int. Cl.
*A61K 36/00* (2006.01)
(52) U.S. Cl. ........................................ 424/734; 424/774
(58) Field of Classification Search ........................ None
See application file for complete search history.

(56) References Cited

U.S. PATENT DOCUMENTS 5,431,997 A * 7/1995 Scott et al. ..................... 442/79

OTHER PUBLICATIONS

Coe et al. (Journal of Ethnopharmacology (1996), vol. 53, pp. 29-50).*
Herbasin.com (http://web.archive.org/web/20060311043152/http://www.herbasin.com/faq.htm—web archived version from Mar. 2006).*
Alecio et al.; "Antifungal Amide from Leaves of *Piper hispidum*"; J Nat Prod. May 1998; 61(5):637-9; [Abstract only—1 pg].
Burke et al.; "Phenylpropene, Benzoic Acid and Flavonoid Derivatives From Fruits of Jamaican *Piper* Species"; Phytochemistry, vol. 25, No. 6, pp. 1427-1430 (1986) [4 pgs].
Friedrich et al.; Abstract; PMID: 15997836 (PubMed-indexed for Medline) [2 pgs], 2005.
Lans et al.; "Medicinal and Ethnoveterinary Remedies of Hunters in Trinidad"; BMC Complementary and Alternative Medicine 2001, 1:10doi:10.1186/1472-6882-1-10 (2001) [13 pgs].
Mesquita; "Essential Oil Constituents of *Piper vicosanum* Yunker From the Brazilian Atlantic Forest"; Journal of Essential Oil Research (Jul./Aug. 2006) [3 pgs].
Sherman; "Medical Encyclopedia: Lithotripsy"; retrieved from http://www.nlm.nih.gov/medlineplus/print/ency/article/007113.htm, on May 16, 2007 (Jul. 2006) [3 pgs].

* cited by examiner

*Primary Examiner*—Susan C Hoffman
(74) *Attorney, Agent, or Firm*—Malloy & Malloy, P.A.

(57) ABSTRACT

A method for treating a patient suffering from kidney and/or urinary system stones including preparing an infusion from a plant, such as, large or medium sized fully-grown *Piper hispidum* leaves, and ingesting a specified amount of the infusion over a predetermined period of time, has proven effective in quickly and painlessly dissolving kidney and/or urinary system stones in the patient. This is a major breakthrough in the field of medical healthcare, eliminating the need for expensive and painful surgery, or other invasive medical procedures, such as, laser treatment(s) or shock wave lithotripsy, which are typically followed by a relatively long recuperative period. By comparison, treatment with an infusion is quick, generally about two to three days, without sophisticated and expensive medical equipment, and without any recuperative period. Furthermore, ingestion of a specified amount of the infusion over a predetermined period of time effectively dissolves kidney and/or urinary system stones allowing the patient to painlessly void the stones in solution with the urine.

19 Claims, 3 Drawing Sheets

METHOD FOR TREATMENT OF KIDNEY AND/OR URINARY SYSTEM STONES

CLAIM OF PRIORITY

The present application is a continuation-in-part patent application of previously filed U.S. patent application having Ser. No. 11/804,185, filed on May 17, 2007, now abandoned which is incorporated herein in its entirety by reference and to which a claim of priority is herein made.

BACKGROUND OF THE INVENTION

1. Field of the Invention

The present application pertains to a method for treating a patient suffering from kidney and urinary system stones via an infusion. More in particular, the present disclosure is directed to a method for preparing an infusion and directing a patient to ingest the infusion in a specified amount over a predetermined period of time. The infusion serves to effectively dissolve the kidney and urinary system stones such that they are easily and readily voided from the patient's body with the patient's urine, thereby eliminating the need for surgery and/or other invasive medical procedures.

2. Description of the Related Art

Research has shown that the genus of plants known as *Piper*, which includes the species *Piper hispidum*, has many medical uses. Folk medicines of the West Indies, Africa, and Latin America, as well as the Indian Ayurvedic system of medicine make use of *Piper* species for healing cough, bronchitis, intestinal pains, wounds, skin irritations and inflammations, according to Mesquita in the Journal of Essential Oil Research in 2006. Among these are *Piper autrium* and *Piper tuberculatum* which, according to Lans in 2001 in BMC Complementary and Alternative Medicine, are used to treat dermatological illnesses in Mexico. Lans also noted that in Puerto Rico and the Caribbean chewed leaves of *Piper amalgo* are put into bleeding cuts and in Guatemala, Panama and Columbia crushed leaves of *Piper* species or the decoction of roots are either ingested or used in baths for snakebites, or rubbed onto the body as a snake repellant. *Piper hispidum* is used in Eastern Nicaragua and Jamaica as a remedy to treat colds, fever, stomachaches and for general aches and pains, once again, according to Lans.

Additionally, research conducted by Felix G. Coe and reported in the Journal of Ethno-Pharmacology in 1996 noted that *Piper hispidum* has several medical applications such as for the treatment of aches and pains, fever and digestive system problems, such as, stomachache, ulcers, etc. The part of the plant tested by Mr. Coe was the leaf, which is the part of the plant utilized in the present method to prepare an infusion which, upon ingestion in a specified amount over a predetermined period of time, effectively dissolves kidney and/or urinary system stones.

Patients suffering from kidney and/or urinary system stones historically have relied upon surgical and/or other invasive medical procedures, such as lasers treatment(s), which result in a long recovery period and/or cause pain to the patient when discharging the partially broken stones out of the body together with the urine. The present method eliminates both the need for surgery and/or other invasive procedures, and the pain associated with discharging the kidney and/or urinary system stones from the body. Specifically, it has been discovered that an infusion prepared from the leaves of *Piper hispidum* and ingested in accordance with the present method effectively dissolves kidney and/or urinary stones such that they are readily and painlessly discharged from the body with the urine.

As stated above, treatment of kidney stones, i.e., renal lithiasis, and/or urinary system stones historically requires patients to ultimately undergo surgery in order to remove the stones. Alternatively, patients have opted to undergo laser treatment(s) or shock wave lithotripsy to break the stones into smaller pieces for discharge from the patient's body. The present invention eliminates the need for such invasive medical treatments for kidney and/or urinary system stones, in particular, preparing an infusion from the leaves of *Piper hispidum* and having a patient ingest a specified amount of the infusion over a predetermined period of time acts to dissolve the kidney and/or urinary system stones such that they may be voided from the patient's body.

The advantages of the present method include a very short treatment period, specifically, only two or three days of treatment are usually required for the kidney and/or urinary system stones to be effectively dissolved. Also, the present method provides relief from the strong pain associated with kidney and/or urinary system stones, such as lower back and stomach pains, soon after a patient ingests the infusion. In addition, and as noted above, the present method eliminates the need for surgery, laser treatments, or any other complicated and invasive medical procedure to remove or reduce the kidney and/or urinary system stones, because the infusion effectively dissolves them such that the patient can painlessly discharge the stones from the body through the urethra together with the patient's urine, thereby providing an easy, fast, painless, and inexpensive procedure for the elimination of kidney and/or urinary system stones from the patient's body.

A further advantage of the present method is that there are no side effects associated with ingesting the infusion, as evidenced via observation of people who have ingested the infusion, and in accordance with previous reports on the use of the *Piper hispidum* plant in which no side effects are known to have been reported. Also important is that the recovery period following ingestion of the infusion, and the dissolution and discharge of the kidney and/or urinary stones is, in most cases, usually between about two to three days, compared to the recovery period following surgery or other invasive procedures which often require weeks or months for full recovery. This is due to the elimination of the extremely invasive kidney and/or urinary system surgery which requires the kidney and/or the portion of the urinary system where the stones are located to be opened and/or enlarged to permit removal, leaving the patient in extreme pain even after the kidney and/or urinary system stones have been removed. It is also noteworthy that the ease of administering the infusion virtually anywhere eliminates the need for a patient to be hospitalized. In fact, the infusion itself is simply ingested instead of water, thereby progressively and dramatically accelerating the rate at which the infusion dissolves kidney and/or urinary system stones. Yet one further benefit of the present method is that the infusion can be used as a preventive measure to avoid recurrence or further development of kidney and/or urinary system stones in patients who suffered from this illness, by drinking approximately one-half gallon, or about seven or eight cups or glasses of the infusion every five to six months. It is noted that when administered as a preventative measure, a patient should drink the infusion instead of the daily potable water intake until about one-half gallon of infusion has been ingested.

SUMMARY

A method for the treatment of a patient having kidney and/or urinary stones includes preparing an infusion from an amount of infusion material, such as, by way of example, all or a portion of a plant, and having the patient ingest a specified amount of the infusion over a predetermined period of time. In at least one embodiment, an infusion material comprises plants of the genus *Piper*, and in one further embodiment, the infusion materials comprise the leaves of *Piper hispidum*. It has been demonstrated that an infusion prepared from the leaves of *Piper hispidum*, in accordance with the present method, and administering the same to a test subject, once again, in accordance with the method disclosed herein, resulted in the subject being cured of kidney stones in a matter of two to three days. The subject had previously been diagnosed with kidney stones and neither found relief nor was the subject able to discharge the kidney stones from the body, despite the fact that the subject took prescribed medication which was intended to enlarge the urethra. The subject then elected to ingest the aforementioned infusion, and the subject began feeling relief almost immediately after drinking the infusion, believed to be due to the initiation of the dissolution process of the kidney stones, which allowed the subject to discharge part of the urine which had been retained in the right kidney due to the presence of the stones.

The subject's kidney stones were effectively dissolved after drinking an infusion prepared from the leaves of *Piper hispidum*, in accordance with the present method, instead of potable water for a period of approximately two days, after which the subject visited a doctor and it was confirmed, via X-ray, that the kidney stones previously present in the subject's right kidney were no longer visible. Several additional subjects, known to be suffering from kidney stones and that had undergone medical treatments which failed to remove the kidney stones and eliminate the strong pain and general discomfort, were treated via the present method. After ingesting an infusion prepared from the leaves of *Piper hispidum*, in accordance with the present method, instead of potable water in the amounts specified herein for a period of approximately three days, each of these additional subjects experienced relief, similar to that experienced by the initial test subject described above.

Although the specific active ingredient(s) contained in *Piper hispidum* which effect dissolution of kidney and/or urinary system stones have yet to be fully isolated and identified, it is evident from the results obtained utilizing the present method that one or more phytochemical or other chemical component present in *Piper hispidum*, either alone or in combination, is responsible for the curative effect of the infusion demonstrated herein. It has, however, been found that the leaves of *Piper hispidum* yield a new pyrrolidine amide, N-[7-(3',4'-methylenedioxyphenyl)-2(Z),4(Z)-heptadienoyl]pyrrolidine 1, in addition to two known amides N-[5-(3',4'-methylenedioxyphenyl)-2(E)-pentadienoyl]pyrrolidine and N-[2-(3',4'-methylenedioxy-6'-methoxyphenyl)-2(Z)-propenoyl]pyrrolidine. Furthermore, 1-Allyl-2,3-(methylenedioxy)-4,5-dimethoxybenzene, 4-methoxy-3,5-bis(3'-methyl-2'-butenyl)-benzoic acid, and the known compounds 5-hydroxy-7-methoxyflavanone and 2,6-1 dihydroxy-4-methoxydihydrochalcone have been isolated from the fruits of Jamaican *Piper aduncum* and *Piper hispidum*. A further study identified three new 4-hydroxy-benzoic acid derivatives: 4-methoxy-3,5-bis-(3-hydroxy-3-methyl-1-butenyl)benzoate; 3-hydroxy-2-(1-hydroxy-1-methylethyl)-2,3-dihydrobenzofuran-5-carboxylic acid; and, 3-hydroxy-2-(1-hydroxy-1-methylethyl)-2,3-dihydrobenzofuran-5-carboxylic acid methyl ester, together with eight known compounds, that were isolated from the stems of *Piper hispidum*.

In at least one embodiment, as noted above, the present method includes the preparation of an infusion from the leaves of *Piper hispidum* for ingestion by a patient. An infusion in accordance with the present method may be prepared as follows. To begin, one must acquire fourteen to sixteen large *Piper hispidum* leaves ranging from about seven to nine and one-half inches in length and ranging from about two to three inches in width. In at least one other embodiment, about twenty-eight to thirty-two medium *Piper hispidum* leaves, ranging in length from about five and one-half to less than seven inches and ranging in width from about one and one-half to two inches, must be acquired. The leaves should be thoroughly rinsed with potable water to remove dirt, soil and any other impurities, as may be required. A clean vessel, such as, for example, a clean pot, is required to boil an amount of potable water of about one gallon. Once the amount of potable water has been poured into the pot, place about fourteen to sixteen large, or twenty-eight to thirty-two medium, previously rinsed leaves of *Piper hispidum* into the pot of potable water. The pot is then heated and its contents, the water and the *Piper hispidum* leaves, are boiled for approximately twenty to twenty-five minutes, thereby forming an infusion. This process is readily and linearly scaled up such that larger volumes of the infusion may be prepared, as long as the amounts of potable water and the recommended amount of large or medium *Piper hispidum* leaves are proportionally maintained.

After boiling for the prescribed amount of time, the source of heat to the pot is removed and the infusion is permitted to cool down to about room temperature. The infusion should have a green color, which could vary from a light green to a more intense green color depending on the size of the leaves that where placed into the pot at the time of boiling. Filtering the infusion, such as via a screen, removes the bulk of the *Piper hispidum* leafy matter as well any loose leaf particles from the liquid phase. The filtered infusion may be stored in any appropriately sized container, such as a plastic container, however, the infusion shall be stored under refrigeration. Even so, however, the infusion should not be stored or ingested after five days of being prepared and refrigerated. The infusion may be ingested cold, i.e., directly from the refrigerator, or it may be allowed to warm to room temperature prior to being ingested.

The infusion itself has a slightly bitter taste, and it has been discovered that adding a teaspoon of honey to approximately one standard cup of the infusion and stirring until the honey is substantially dissolved in the infusion makes the infusion more palatable to the patient, and has proven not to negatively impact its curative effect. The addition of any other natural or artificial sweetener to the infusion is not recommended. The addition of honey to the infusion is the patient's choice, and this decision should be based on the patient's condition and his or her ability to properly digest the additional amount of sugar(s) present in the honey, as well as any allergies or other negative impacts to the patient as a result of ingesting honey.

The patient should drink the infusion wherein a single dosage of the infusion comprises a standard cup or glass containing approximately eight fluid ounces of the infusion. In at least one embodiment, the patient should drink about six to eight of the aforementioned single dosages of the infusion per day, substituting the infusion for the normal daily intake of water for an average person, for a period of time of between about two or three days.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION

Figure 1:
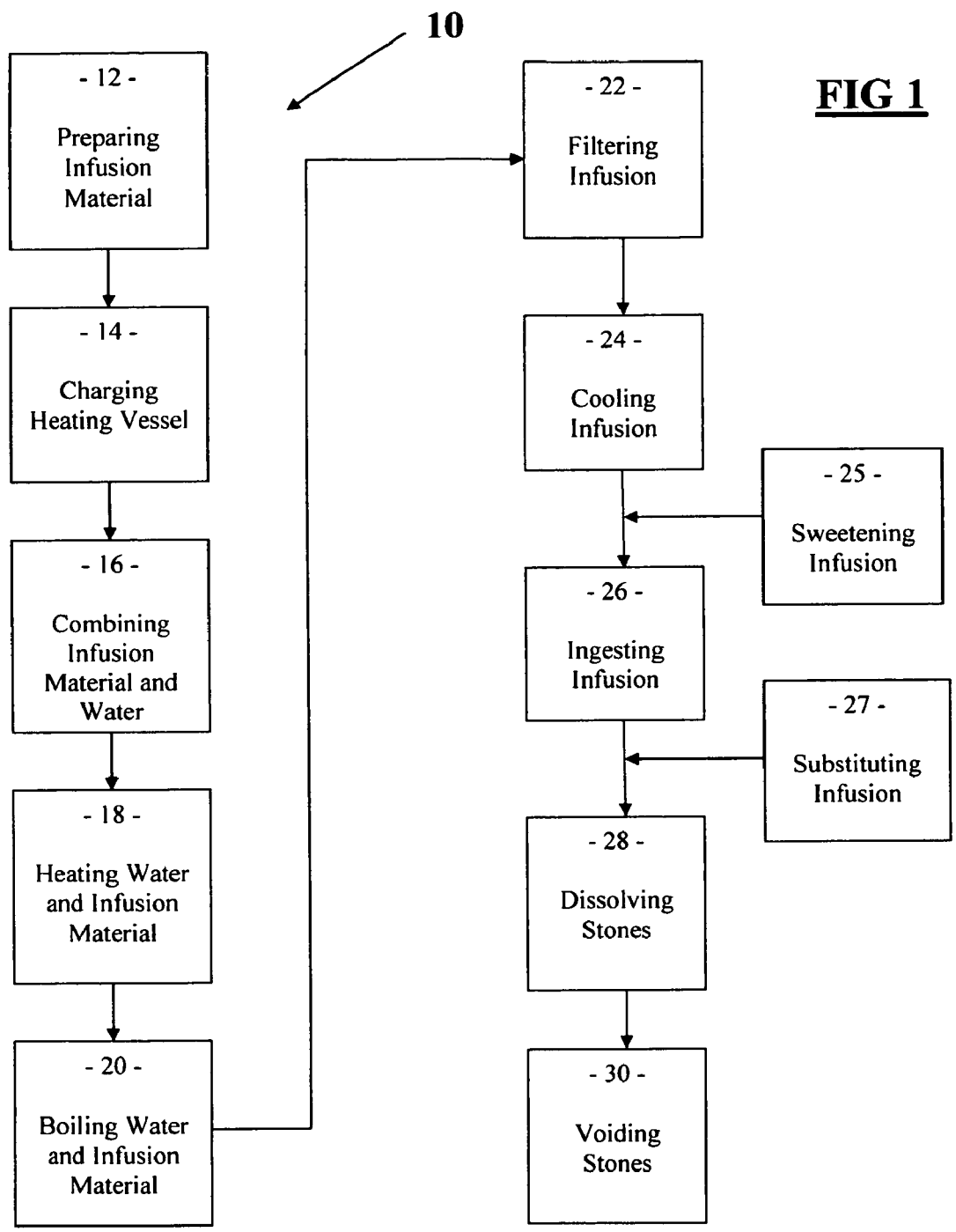
FIG. 1 is a diagrammatic representation of one embodiment of a method for treatment of a patient having kidney and/or urinary system stones in accordance with the present specification.

As noted above, the present specification is directed to a method 10 for treating a patient having kidney and/or urinary system stones as shown in FIG. 1. In general, the present method 10 comprises preparing an infusion and having a patient ingest a specified amount of the infusion over a predetermined period of time. The infusion acts to effectively dissolve the kidney and/or urinary system stones after about two to three days thereby permitting the patient to void the stones with the urine.

Figure 2:
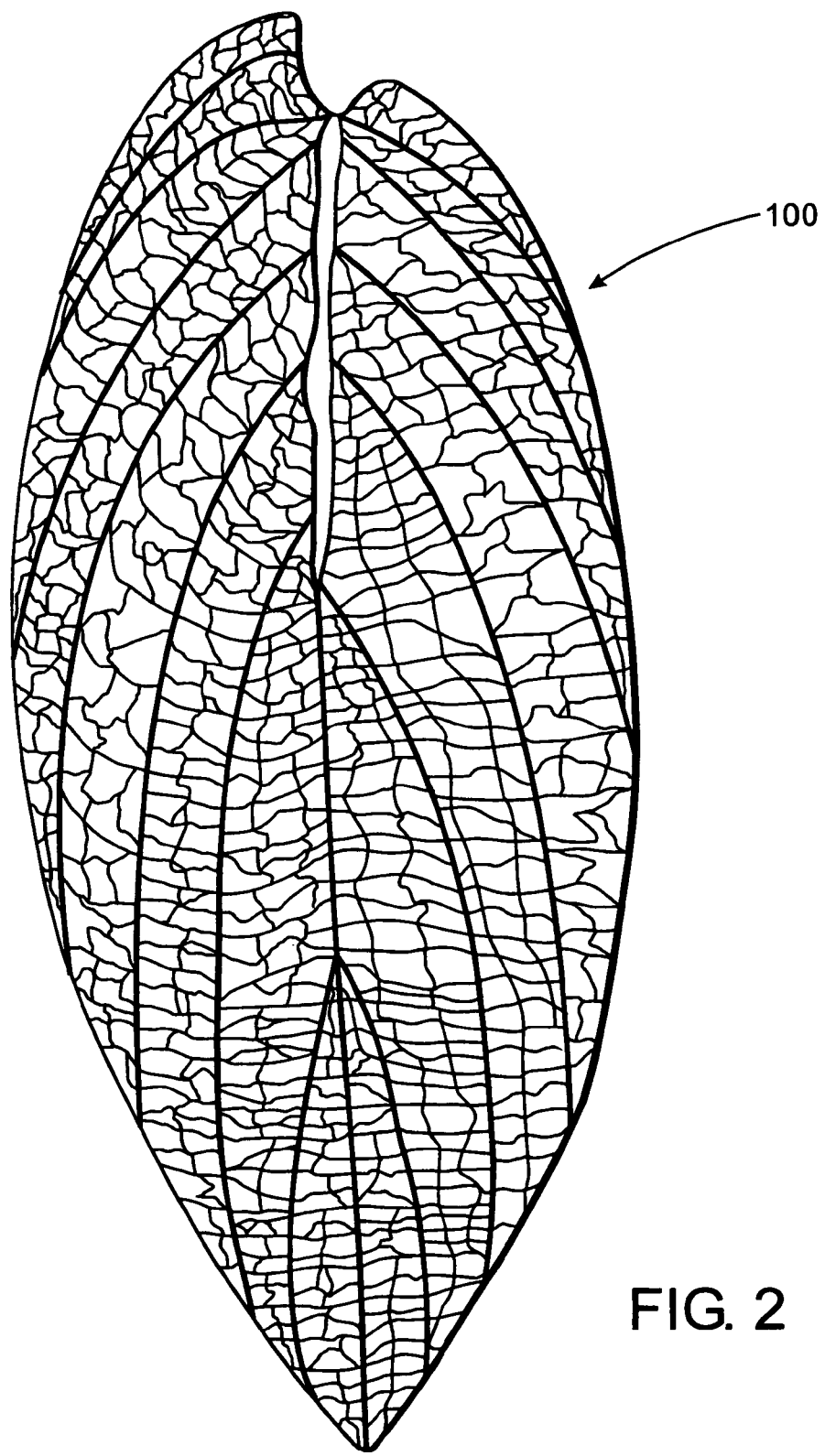
FIG. 2 is an illustration of a leaf of a *Piper hispidum* plant.

To begin, the present method requires obtaining and preparing an appropriate amount of an infusion material 12. As noted above, the infusion material may comprise all or a portion of a plant. As further noted above, in at least one embodiment, the infusion material comprises plants of the genus *Piper*, and in one further embodiment, the infusion material comprises large or medium sized fully-grown leaves of *Piper hispidum*. FIG. 2 is illustrative of a fully-grown leaf of *Piper hispidum* 100.

In one illustrative embodiment of the present method 10, the infusion material comprises about fourteen (14) to sixteen (16) large *Piper hispidum* leaves ranging in length from about seven (7) to nine and one-half (9½) inches and ranging in width from about two (2) to three (3) inches. The foregoing dimensions are representative of large *Piper hispidum* leaves, and include only the leaf, not the inflorescences located with the leaves. In another illustrative embodiment of the present method 10, the infusion material comprises about twenty-eight (28) to thirty-two (32) medium *Piper hispidum* leaves ranging in length from about five and one-half (5½) to less than seven (7) inches and ranging in width from about one and one-half (1½) to two (2) inches. Preparing 12 the infusion material includes washing and/or rinsing the infusion material, for example, large or medium *Piper hispidum* leaves, with potable water to remove soil, dirt and other impurities which may be present.

In addition, the present method 10 requires charging 14 a heating vessel, for example, a clean pot, with an amount of an extraction fluid. In at least one embodiment, potable water is utilized as the extraction fluid, and the present method 10 comprises charging 14 the heating vessel with about one (1) gallon of potable water, and combining 16 the infusion material, i.e., about fourteen to sixteen large *Piper hispidum* leaves, with the amount of potable water thereby forming a mixture in the heating vessel.

Once the infusion material and the extraction fluid have been combined in the heating vessel, such as in the foregoing illustrative example, wherein fourteen to sixteen large *Piper hispidum* leaves are combined with about one gallon of potable water, the present method 10 comprises heating 18 the mixture in the heating vessel to the point at which the mixture boils. Further, the present method 10, in at least one embodiment, includes boiling 20 the water and infusion material mixture for an amount of time ranging from about twenty (20) to twenty-five (25) minutes, thereby forming an infusion. Of course, it is understood to be within the scope and intent of the present invention to utilize a longer or shorter boiling period, depending on the infusion material, extraction fluid, relative proportions of each in the heating vessel, as well as the configuration of the heating vessel, all of which may impact the amount of boiling required to extract the active component(s) from the infusion material into the extraction fluid such that an effective infusion is prepared.

After the mixture of infusion material and extraction fluid, such as, by way of example, *Piper hispidum* leaves and potable water, have been boiling 20 for the prescribed period of time, the source of heat is removed from the heating vessel and the resulting infusion is permitted to begin to cool. The infusion color at this stage may vary from a light green to a more intense green color depending, at least on part, on the number and size of the *Piper hispidum* leaves placed into the mixture. The intensity of the green color of the infusion does not necessarily define its effectiveness, it is merely a characteristic of the infusion after boiling the above-referenced mixture for a period of about twenty (20) to twenty-five (25) minutes.

In at least one embodiment, the present method 10 further comprises filtering 22 the mixture of infusion material and extraction fluid after boiling, in order to remove bulk solids from the resulting infusion. As one example, the present method 10 employs a screen through which the mixture of *Piper hispidum* leaves and potable water are passed, after boiling, to remove *Piper hispidum* leaves and leaf particles from the infusion.

After filtering 22, the infusion is transferred into a clean, appropriately sized container, and in at least one embodiment, cooling 24 of the infusion is accomplished via storage under refrigeration. In at least one alternate embodiment, cooling 24 is accomplished by allowing the infusion to remain in the container under ambient conditions until the temperature of the infusion is essentially the same as room temperature, i.e., about 70 to 80 degrees Fahrenheit, prior to refrigeration for storage. In this alternate embodiment, at least a portion of the infusion may be retained at room temperature for immediate ingestion by a patient. In yet one further embodiment, a heat exchanger is utilized to facilitate cooling of the infusion, such as is particularly useful when large volumes of infusion are being prepared.

An infusion of *Piper hispidum* prepared in accordance with the present method 10 will often taste bitter and unpleasant to many persons. As such, the present method 10 provides an optional step of sweetening 25 the infusion to make it more palatable to the patient for ingestion, as is illustrated in FIG. 1. In one embodiment, sweetening 25 the infusion is accomplished by the addition of about one teaspoon of honey to one standard cup of the infusion and stirring until the honey is substantially dissolved in the infusion. The use of about one teaspoon of honey per standard cup of infusion has proven effective in improving the palatability of the infusion, without adversely affecting its curative effects. The addition of honey to the infusion is strictly the patient's choice to facilitate the ingestion process, however, the patient's ability to process the amount of sugar(s) present in the honey, as well as any allergies and/or other negative impacts to the patient's condition by ingesting honey, must be taken into consideration.

Once the infusion has been cooled to room temperature, or cooler, the present method 10 includes the patient ingesting 26 a specified amount of the infusion over a predetermined period of time. In at least one embodiment, the present method 10 provides for the patient ingesting 26 a specified amount of about six to eight standard cups or glasses of the infusion daily, and the patient substituting 27 the specified amount of the infusion for the patient's normal daily intake of potable water, i.e., six to eight standard cups of potable water daily, wherein a standard cup as used herein comprises about eight fluid ounces. The patient should substitute the infusion in standard cups or glasses which are about the same size as that recommended for daily potable water intake, i.e., about eight fluid ounces per standard cup or glass. Since a major component of the infusion, in at least one embodiment, is water, substituting 27 the infusion for the daily potable water intake accelerates the infusions curative effects. Typically, a patient will begin to feel relief from the strong pain caused by the kidney and/or urinary system stones shortly after drinking an amount of the infusion. In this embodiment, the patient should ingest the specified amount of infusion for a period of time ranging from about two to three days.

Upon ingesting 26 the infusion it begins dissolving 28 the patient's kidney and/or urinary system stones until the stones are effectively dissolved. Thus, the present method 10 thereby facilitates voiding 30 the kidney and/or urinary system stones from the patient's body easily and painlessly as they become effectively dissolved in the patient's urine. It is noted that, depending on the size and number of the kidney and/or urinary system stones and the frequency of ingesting the infusion, a period of time of greater than three days may be required to effectively dissolve the kidney and/or urinary system stones to facilitate voiding 30 them from the patient's body.

In the event an additional amount of infusion is required to dissolve all the kidney and/or urinary system stones, once again, depending on the size and number of stones present in the patient, the foregoing steps may be repeated to prepare additional amounts of infusion. Alternatively, a larger volume of infusion may be prepared initially by simply maintaining the relative proportions of infusion material and extraction fluid, as disclosed herein. As just one example, the amount of infusion prepared may be essentially doubled by combining 16 about twenty-eight (28) to thirty-two (32) large *Piper hispidum* leaves, or about fifty-six (56) to sixty-four (64) medium *Piper hispidum* leaves, with about two gallons of potable water, followed by heating 18, boiling 20, filtering 22, and cooling 24, in accordance with the present method 10. As one further example, a significant amount of infusion may be prepared, such as may be required for treatment of a plurality of patients suffering from kidney and/or urinary system stones, by combining 16 about one-thousand and four-hundred (1,400) to one-thousand and six-hundred (1,600) large *Piper hispidum* leaves, or about two-thousand and eight hundred (2,800) to three-thousand and two-hundred (3,200) medium *Piper hispidum* leaves, with about one-hundred (100) gallons of potable water, followed by heating 18, boiling 20, filtering 22, and cooling 24, once again, in accordance with the present method 10. In order to meet the anticipated demand for infusion prepared in accordance with the present method 10 across the United States, mass production of infusion prepared from *Piper hispidum* leaves will be required, after which, the infusion may be refrigerated and shipped in appropriately sized containers for individual usage, for example, one-half gallon and/or one gallon containers. As noted above, however, the infusion of *Piper hispidum* prepared in accordance with the present method 10 should be stored and/or ingested within five days of preparation, after which time, it should be discarded.

Figure 3:
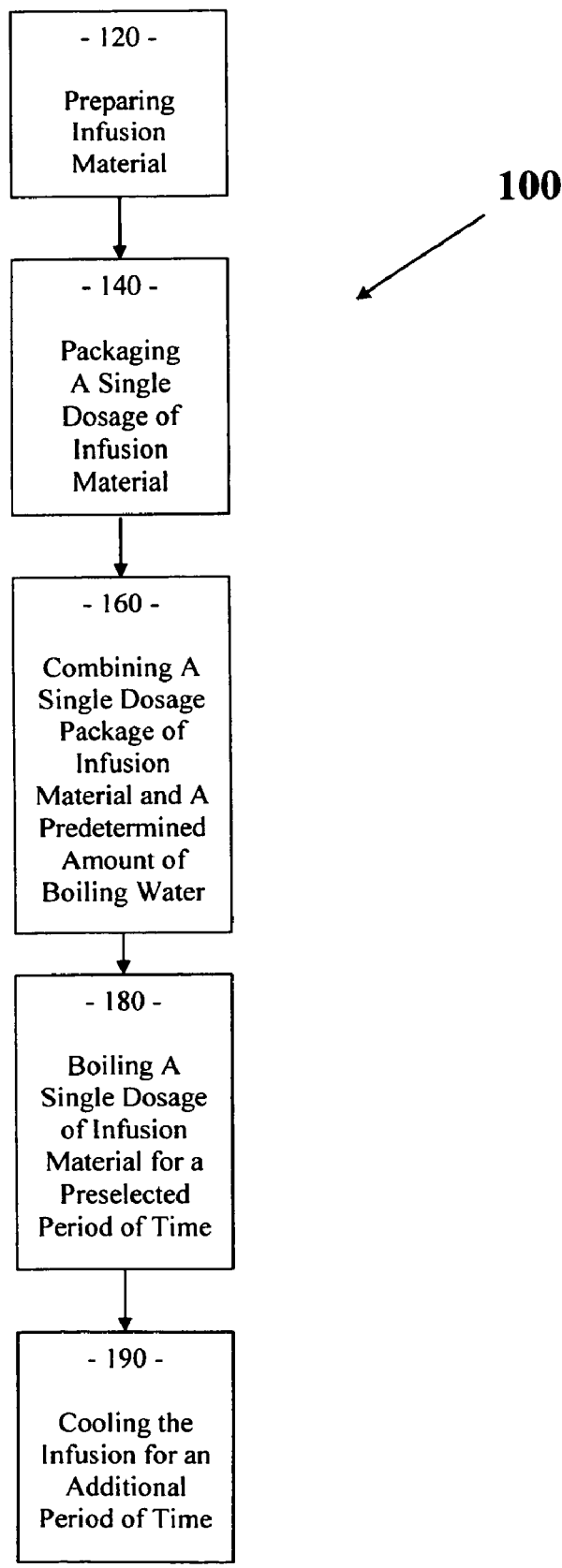
FIG. 3 is a diagrammatic representation of one method for preparing a single dosage of an infusion for treatment of a patient having kidney and/or urinary system stones in accordance with the present specification.

FIG. 3 is illustrative of a method 100 for preparing a single dosage of an infusion in accordance with the present specification. To begin, and as in the previously disclosed method 10, the method 100 requires preparing 120 infusion material which, as above, may comprise all or a portion of a plant, for example, large or medium sized fully-grown leaves of *Piper hispidum*. Also as above, preparing 120 the infusion material includes washing and/or rinsing the infusion material, for example, large or medium *Piper hispidum* leaves, with potable water to remove soil, dirt and other impurities which may be present.

The method 100 further comprises packaging 140 a single dosage of infusion material in such a manner that the infusion material is ready to be combined with an appropriate amount of boiling liquid, for example, eight ounces of boiling potable water. As one example, packaging 140 a single dosage of infusion material comprises packaging one (1) large *Piper hispidum* leaf, which has been rendered into a plurality of small pieces by chopping, cutting, or grinding, so as to facilitate the extraction process, and enclosing the single dosage of infusion material in a single dosage package, such as, by way of example, a flow through teabag type configuration. As one other example, packaging 140 a single dosage of infusion material comprises packaging two (2) medium *Piper hispidum* leaves which have been rendered into a plurality of small pieces, and enclosing the single dosage of infusion material in a water permeable single dosage package. The single dosage package in accordance with the present method 100 is structured to permit liquid to freely flow in and out, so as to facilitate extraction, yet comprises a fine enough filtering medium to retain a substantial portion of the pieces of infusion material therein.

As illustrated in FIG. 3, the present method 100 further includes combining 160 the single dosage package of infusion material and a predetermined amount of boiling water, and in at least one embodiment, boiling potable water. Consistent with the previously disclosed method, a single dosage of the present infusion comprises a standard eight fluid ounce cup or glass of the infusion. As such, the predetermined amount of boiling water in accordance with at least one embodiment of the present method 100 is an amount of eight fluid ounces. The present method 100 further comprises boiling 180 the single dosage of infusion material for a preselected period of time. In at least one embodiment, the preselected period of time is between about 7 to 8 minutes, thereby forming an infusion. After boiling 180 the single dosage of infusion material for the preselected period of time, at least one embodiment of the present method 100 includes cooling 190 the resultant infusion to room temperature while the single dosage package of infusion material remains in the infusion for an additional cooling period. This additional cooling period assures sufficient extraction of phytochemicals and/or other chemical components from the infusion material into the infusion itself.

Once the single dosage of infusion material has been boiled in boiling water for the preselected period of time and cooled to about room temperature, the single dosage package may be removed and drained into the cup or glass, and the infusion ingested in accordance with the daily dosage schedule previously presented. In addition, the infusion may be sweetened with honey, as previously described. As will be appreciated, the method 100 for preparing a single dosage of infusion presents a convenient alternative to those persons who may be incapable or simply are not motivated enough to prepare a larger volume of infusion as is required for ingestion by a patient for a period of several days.

The present methods 10 and 100 are unlike anything else available for the treatment of patients suffering from kidney and/or urinary system stones. As previously stated, the currently available kidney and/or urinary system stone treatments consists of invasive surgery, laser treatment(s), shock wave lithotripsy and/or prescribed medications which are designed to enlarge the urethra. The first two of these treatments require relatively long patient recuperation periods and are expensive and painful procedures. In addition, lithotripsy, depending on the size of the stones, may lead to complications such as damage to the kidney and/or other nearby tissue, such as, the stomach area, and some patients are at greater risk than others to lithotripsy treatment, according to Sherman in 2006 in the Medical Encyclopedia: Lithotripsy. On the other hand, the medications prescribed to enlarge the urethra in most cases fail to allow larger kidney stones to be discharged therethrough with the urine and, additionally, smaller stones which do pass through the urethra often cause considerable pain and in some cases may even inflict small internal cuts as they are voided from the body.

The present invention enhances the quality of life of those suffering from kidney and/or urinary system stones, by initially reducing and ultimately eliminating the pain associated with kidney and/or urinary system stones as the treatment progresses in a shorter amount of time while lowering the cost of treatment when compared to the procedures that are currently employed. Further, as noted above, utilization of either of the present methods 10 or 100 does not result in any known side effects. As just one example, patients with kidney and/or urinary system stones do not require surgical or other invasive medical procedures, therefore, the typically long recuperative period of weeks, or even months, is eliminated. Utilizing the present method 10, a patient may experience almost immediate relief from the pain and suffering of the kidney and/or urinary system stones, as soon as the specified amount of infusion is ingested. Further, after only two to three days of ingesting the specified amount of the infusion, the kidney and/or urinary system stones are effectively dissolved and may be discharged from the body with the urine. The present method provides a treatment option which is significantly more economical than existing or available treatments for patients afflicted with kidney and/or urinary system stones. More in particular, existing treatment options require sophisticated medical equipment and procedures, prescribed medication, and/or hospital stay, whereas the present method 10 merely comprises preparing and ingesting a specified amount of an infusion over a predetermined period of time, as previously indicated, after which the patient can fully resume normal daily activities, with no medical complications.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

Now that the invention has been described,

What is claimed is:

1. A method for treatment of a patient having kidney or urinary system stones, the method comprising:
preparing an amount of *Piper hispidum* leaves,
charging a heating vessel with an amount of potable water,
combining the amount of *Piper hispidum* leaves with the amount of potable water in the heating vessel to form a mixture,
heating the mixture in the heating vessel to the point of boiling,
boiling the mixture in the heating vessel for a period of time thereby forming an infusion,
filtering the mixture to remove the *Piper hispidum* leaves and portions thereof from the infusion,
cooling the infusion,
ingesting a specified amount of the infusion over a predetermined period of time, the infusion dissolving the kidney or urinary system stones into the patient's urine, and
voiding the dissolved kidney or urinary system stones from the patient's body with the urine.

2. The method as recited in claim 1 wherein preparing the amount of *Piper hispidum* leaves comprises washing the amount of *Piper hispidum* leaves with potable water.

3. The method as recited in claim 2 wherein the amount of *Piper hispidum* leaves includes a plurality of large *Piper hispidum* leaves each comprising a length of about seven to nine and one-half inches.

4. The method as recited in claim 2 wherein the amount of *Piper hispidum* leaves includes a plurality of large *Piper hispidum* leaves each comprising a width of about two to three inches.

5. The method as recited in claim 2 wherein charging the heating vessel with an amount of potable water comprises charging the heating vessel with about one gallon of potable water.

6. The method as recited in claim 1 wherein boiling the mixture for a period of time comprises boiling the mixture for between about twenty to twenty-five minutes.

7. The method as recited in claim 1 wherein ingesting the specified amount of the infusion comprises the patient ingesting about six to eight standard cups of the infusion per day.

8. The method as recited in claim 1 wherein ingesting the specified amount of the infusion over the predetermined period of time comprises the patient ingesting the specified amount of the infusion over about two to three days.

9. A method for treatment of a patient having kidney or urinary system stones, the method comprising:
preparing a plurality of medium *Piper hispidum* leaves by washing with potable water, wherein the medium *Piper hispidum* leaves comprise a length of about five and one-half to less than seven inches and a width of about one and one-half to two inches,
charging a vessel with about one gallon of potable water,
combining the plurality of medium *Piper hispidum* leaves with the potable water to form a mixture,
heating the mixture to the point of boiling,
boiling the mixture for about twenty to twenty-five minutes, thereby forming an infusion,
cooling the infusion to about room temperature,
ingesting a specified amount of the infusion over a predetermined period of time, the infusion dissolving the kidney or urinary system stones into the patient's urine, and
voiding the dissolved kidney or urinary system stones from the patient's body with the urine.

10. The method as recited in claim 9 wherein combining the plurality of medium *Piper hispidum* leaves with the potable water to form a mixture comprises combining about twenty-eight to thirty-two medium *Piper hispidum* leaves with the potable water.

11. The method as recited in claim 9 further comprising sweetening the specified amount of the infusion prior to ingesting.

12. The method as recited in claim 10 wherein sweetening the specified amount of the infusion comprises adding about one teaspoon of honey to one standard cup of the infusion and stirring until the honey is substantially dissolved in the infusion.

13. The method as recited in claim 10 wherein ingesting the specified amount of the infusion comprises the patient ingesting about six to eight standard cups of the infusion per day.

14. The method as recited in claim 10 wherein ingesting the specified amount of the infusion over the predetermined period of time comprises the patient ingesting the specified amount of the infusion over about two to three days.

15. A method for the treatment of a patient having kidney or urinary system stones, the method comprising:
preparing about fourteen to sixteen large *Piper hispidum* leaves, wherein the large *Piper hispidum* leaves comprise a length of about seven to nine and one-half inches, and a width of about two to three inches,
charging a heating vessel with about one gallon of potable water,
combining the large *Piper hispidum* leaves with the amount of potable water in the heating vessel to form a mixture,
heating the mixture in the heating vessel to the point of boiling, boiling the mixture in the heating vessel for about twenty to twenty-five minutes, thereby forming an infusion, filtering the mixture to remove the large *Piper hispidum* leaves and portions thereof, cooling the infusion to at least about room temperature, ingesting a specified amount of the infusion over a predetermined period of time such that the infusion dissolves the kidney or urinary system stones into the patient's urine, and voiding the kidney or urinary system stones from the patient's body with the patient's urine.

16. The method as recited in claim 15 wherein ingesting the specified amount of the infusion comprises the patient ingesting about six to eight standard cups of the infusion per day.

17. The method as recited in claim 15 wherein ingesting the specified amount of the infusion over the predetermined period of time comprises the patient ingesting the specified amount of the infusion over about two to three days.

18. The method as recited in claim 15 further comprising the patient substituting the specified amount of the infusion, wherein the specified amount of the infusion comprises about six to eight standard cups of the infusion per day, for the patient's daily intake of potable water.

19. The method as recited in claim 16 wherein ingesting the specified amount of the infusion over the predetermined period of time comprises the patient ingesting the specified amount of the infusion over about two to three days.

* * * * *